(12) United States Patent
Schlienger et al.

(10) Patent No.: US 8,906,024 B2
(45) Date of Patent: *Dec. 9, 2014

(54) INTRAMEDULLARY NAIL

(75) Inventors: Andre Schlienger, Basel (CH); Markus Buettler, Oensingen (CH); Robert Frigg, Bettlach (CH)

(73) Assignee: Depuy Synthes Products, LLC, Raynham, MA (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/592,887

(22) Filed: Aug. 23, 2012

(65) Prior Publication Data

US 2012/0323240 A1 Dec. 20, 2012

Related U.S. Application Data

(63) Continuation of application No. 11/823,766, filed on Jun. 27, 2007, now Pat. No. 8,262,658, which is a continuation of application No. PCT/CH2004/000758, filed on Dec. 31, 2004.

(51) Int. Cl.
*A61B 17/72* (2006.01)
*A61B 17/86* (2006.01)

(52) U.S. Cl.
CPC ............. *A61B 17/72* (2013.01); *A61B 17/7283* (2013.01); *A61B 17/8635* (2013.01)
USPC .......................................................... 606/64

(58) Field of Classification Search
USPC ...................................... 606/62–68
See application file for complete search history.

(56) References Cited

U.S. PATENT DOCUMENTS

| | | | | |
|---|---|---|---|---|
| 4,055,172 A | * | 10/1977 | Ender et al. | 606/62 |
| 4,135,507 A | * | 1/1979 | Harris | 606/62 |
| 4,169,470 A | * | 10/1979 | Ender et al. | 606/62 |
| 4,475,545 A | * | 10/1984 | Ender | 606/64 |
| 4,503,847 A | * | 3/1985 | Mouradian | 606/64 |
| 4,919,673 A | * | 4/1990 | Willert et al. | 623/23.48 |
| 5,041,115 A | * | 8/1991 | Frigg et al. | 606/62 |
| 6,010,506 A | * | 1/2000 | Gosney et al. | 606/62 |
| 6,120,504 A | * | 9/2000 | Brumback et al. | 606/62 |
| 6,461,360 B1 | * | 10/2002 | Adam | 606/67 |
| 8,317,788 B2 | * | 11/2012 | Kaup | 606/62 |
| 2002/0099379 A1 | * | 7/2002 | Adam | 606/67 |
| 2002/0183750 A1 | * | 12/2002 | Buhler | 606/62 |

* cited by examiner

*Primary Examiner* — Jerry Cumberledge
(74) *Attorney, Agent, or Firm* — Fay Kaplun & Marcin, LLP

(57) ABSTRACT

An intramedullary nail includes an elongated body extending along a central longitudinal axis. The intramedullary nail includes a straight proximal end portion along with a straight distal end portion extending proximally from a distal end of the nail by a predetermined length and a central portion extending proximally from a proximal end of the distal end portion to a distal end of the proximal end portion. The central portion includes a first curved portion having a first length with a first radius of curvature and a second curved portion having a second length shorter than the first length and a second, non-zero radius of curvature smaller than the first radius of curvature.

20 Claims, 1 Drawing Sheet

INTRAMEDULLARY NAIL

CROSS REFERENCE TO RELATED APPLICATION

The present application is a Continuation Application of U.S. patent application Ser. No. 11/823,766 filed on Jun. 27, 2007 now U.S. Pat. No. 8,262,658, which is a Continuation application of PCT Appln. Serial No. PCT/CH2004/000758 filed on Dec. 31, 2004. The disclosures of the above applications are incorporated herein by reference.

TECHNICAL FIELD

The invention relates to an intramedullary nail, particularly for use in the tibia.

BACKGROUND OF THE INVENTION

U.S. Pat. No. 6,010,506 to GOSNEY describes a generic intramedullary nail. The intramedullary nail has a proximal end part which can be pressed on, and a distal end part. The proximal end and the distal end are at an angle relative to one another by means of several curved segments which are disposed between the end parts. In addition, the proximal end part is bent at right angles so that a relatively large angle is formed between the tangents to the central axes at the axial ends. A disadvantage of this known intramedullary nail that it is not suitable for use in relatively linear, tubular bones, especially the tibia.

SUMMARY OF THE INVENTION

The present invention is to provide a remedy for the above-discussed disadvantage. It is an object of the invention to produce an intramedullary nail having a central section comprising of several curved sections. The tangents at the two end points of this central section encloses a relatively small angle. That is, an angle which is suitable particularly for linear, tubular bones.

Pursuant to the invention, this objective is accomplished with an intramedullary nail having a proximal end part, a distal end part, and a central section. The central section includes a first curved section having a first length with a first radius of curvature, and a second curved section having a second length shorter than the first length and a second radius of curvature smaller than the first radius of curvature. The intramedullary nail also includes a central axis. Tangents at two end points of the central section, including the first and second curved sections, enclose an angle gamma between about 9° and about 12°. The intramedullary nail may have a total length ranging from 200 to 500 mm.

Some advantages achieved by the intramedullary nail of this application are that:

the intramedullary nail having a central section comprising of two curved sections, because of the two curvatures, which have a different radius, the intramedullary nail can be adapted optimally to a medullary canal;

the tangents at the end points of the central section enclose an angle gamma of between 9° and 12° such that the intramedullary nail is suitable for relatively linear tubular bones, especially for the tibia, and because of the small angle gamma, it is possible to insert the intramedullary nail into a medullary space without using much force.

In different embodiments, the intramedullary nail may have the following distinguishing features:

the length of the proximal end part $G_3$ ranges from ⅙ L to ⅓ L, where L is the total length of the intramedullary nail;

the tangents at the two end points of the first curved section enclose an angle alpha ranging from about 7° to about 10°, and preferably from about 8° to about 9°;

the tangents at the two end points of the second curved section enclose an angle beta ranging from about 1° to about 3°;

the first curved end section of length $G_1$ has a radius of curvature $R_1$ ranging from about 300 to about 1,300 mm;

the ratio of the total length of the intramedullary nail to the radius of the curvature of the first curved section ($L/R_1$) ranges from about 0.2 to about 0.8;

the length (l) of the straight, distal part ranges from about 0.20 L to about 0.55 L, and preferably from about 0.25 to about 0.50 L;

the length $G_1$ of the first curved section ranges from about 0.2 L to about 0.4 L; and the radius of curvature $R_2$ of the second curved section ranges from about 10 mm to about 50 mm.

In a further embodiment, the proximal end part axially adjoins the second curved section and is formed as a straight proximal section.

In still a different embodiment, the distal end part is constructed as a straight section.

Due to the formation of one or both end parts as straight sections, an advantage can be attained that the curvature of the intramedullary nail is slight. As a result, the intramedullary nail is particularly suitable for straight, tubular bones.

In a further embodiment, the intramedullary nail may have a longitudinal borehole which is coaxial with the central axis.

In yet another embodiment, there may be at least one locking hole which extends transversely to the central axis and is suitable for accommodating a screw, in the region of the proximal end part.

In a further embodiment, there may be at least one locking hole, extending transversely to the central axis and is also suitable for accommodating a screw, in the region of the distal end part.

In yet a further embodiment, there may be two locking holes, extending transversely to the central axis and enclose with one another an angle preferably of about 45° to about 90°, in the region of the distal end part.

In another embodiment, the distal end part may have four locking holes. The distance of the proximally located central locking hole to the other two locking holes may be different.

An implantation method of a cannulated intramedullary nail may include the following steps:

Step A: Bringing about and maintaining the optimum setting, depending on the type of fracture;

Step B: Opening the medullary canal with the help of an opening instrument so that the entry angle and the orientation with respect to the medullary canal are correct, depending on the surgical technique used;

Step C: Introducing a guide wire up into the distal, future end position of the intramedullary nail and determining the length of the intramedullary nail required;

Step D: The intramedullary nail, pre-mounted on the insertion handle, is brought by means of the guide wire through the opening channel into the medullary space;

Step E: After the axial position of the intramedullary nail is checked and repositioned, the intramedullary nail is locked into place by one of various locking options.

BRIEF DESCRIPTION OF THE DRAWINGS

The intramedullary nail is explained in even greater detail in the following exemplary drawings. The intramedullary nail may be better understood by reference to the following drawings, wherein like references numerals represent like elements. The drawings are merely exemplary to illustrate the structure, operation and method of use of the intramedullary nail and certain features that may be used singularly or in combination with other features and the invention should not be limited to the embodiments shown.

DESCRIPTION OF THE PREFERRED EMBODIMENTS

Figure 1:
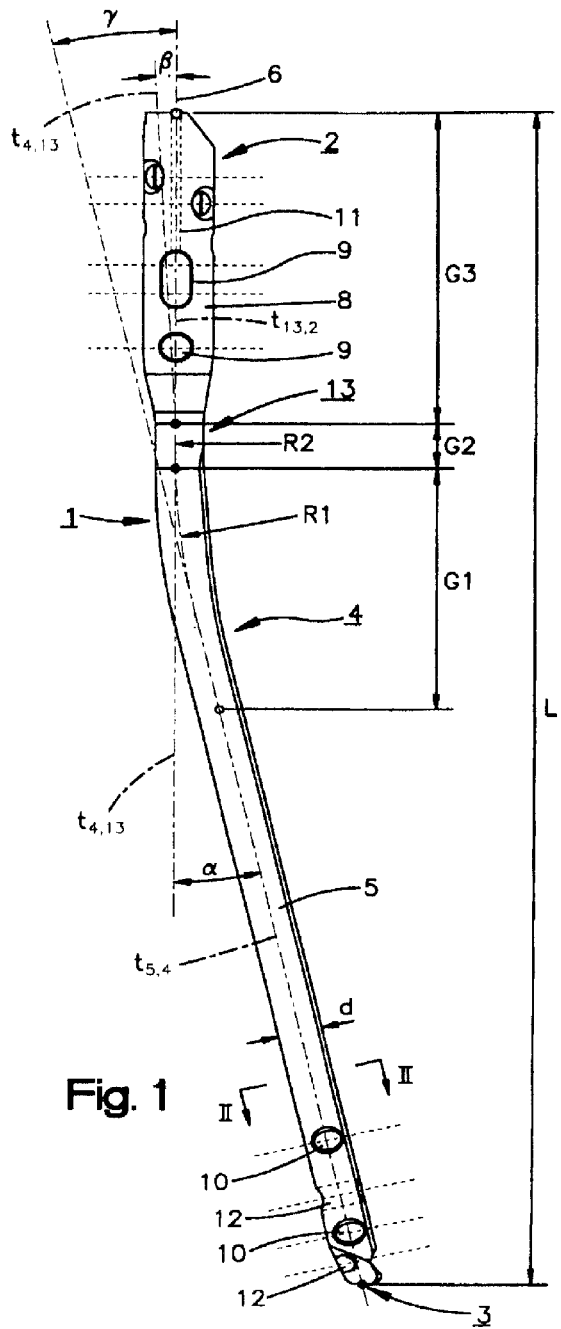
FIG. 1 shows a longitudinal section through an embodiment of the inventive intramedullary nail.
Figure 3:
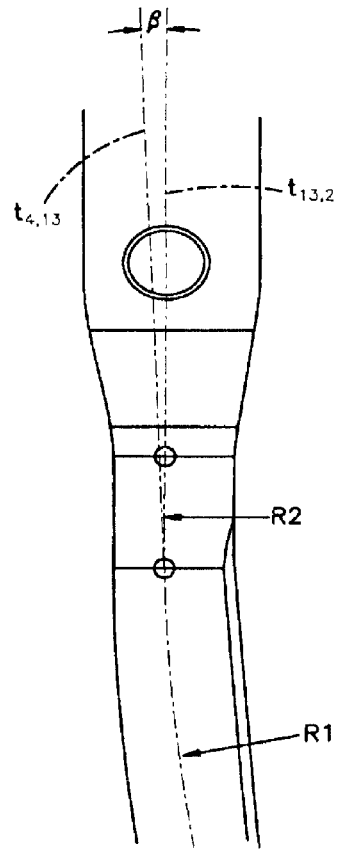
FIG. 3 shows an enlarged section in the region of the second, curved section of the embodiment of the inventive intramedullary nail shown in FIGS. 1 and 2.
Figure 2:
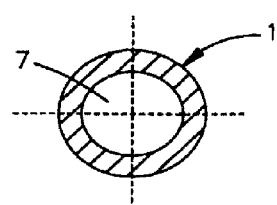
FIG. 2 shows a section along the line II-II of FIG. 1.

The intramedullary nail 1, shown in FIGS. 1 to 3, may comprise a central axis 6, a proximal end part 2, a distal end part 3 that is suitable for introduction into the intramedullary space and two curved sections 4; 13 disposed axially one behind the other. The total length of the intramedullary nail "L" ranges from about 200 mm to about 500 mm. Axially, the proximal end part 2 adjoins the second, curved section 13 and is constructed as a straight, proximal section 8 of length $G_3$. Length $G_3$ may be less than or equal to the total length L of the intramedullary nail and preferably ranges between about ⅙ L to about ⅓ L. The distal end part 3 may be constructed as a straight, distal section 5 with a length "l" ranging from about 0.20 L to about 0.55 L, and preferably from about 0.25 L to about 0.50 L. The first curved section 4 may have a length $G_1$ that is less than or equal to L, and preferably ranges from about 0.2 L to about 0.4 L. The first curved section may have a radius of curvature $R_1$ ranging from about 300 mm to about 1,300 mm, where a ratio between the total length of the intramedullary nail and the radius of the curvature ($L/R_1$) is between about 0.2 to about 0.8. The second curved section 13, disposed between the proximal end part 2 and the first curved section 4, may have a length $G_2$ which may be less than or equal to length $G_1$, and a radius curvature $R_2$ which may be less than $R_1$. Preferably the radius of curvature $R_2$ ranges from about 10 mm to about 50 mm. Tangents $t_{5,4}$ and $t_{13,2}$ at the two end points of a middle section, enveloping the two curved sections 4; 13, enclose an angle gamma of about 9° to about 12°, and preferably about 10° and coincide proximally with the central axis 6 of the straight, proximal section 8 and distally with the central axis 6 of the straight, distal section 5. Furthermore, the tangents $t_{5,4}$ and $t_{4,13}$ at the two end points of the first curved section 4 enclose an angle alpha of about 7° to about 10°, and preferably from about 8° to about 9°. The tangents $t_{4,13}$ and $t_{13,2}$ at the two end points of the second curved section 13 enclose an angle beta of about 1° to about 3°, and preferably about 2°.

Both curvatures of the intramedullary nail lie in the plane of the drawing, which, after the implantation of the intramedullary nail 1, corresponds to the anatomical medio-lateral plane. That is, the intramedullary nail, when implanted, is bent in the antero-posterior direction.

The intramedullary nail may have a continuous longitudinal borehole 7 which is coaxial with the central axis 6 (see FIG. 2).

In the region of the proximal end part 2 of the intramedullary nail 1, there may be one to four locking holes 9 which extend transversely to the central axis 6. One of the four locking holes 9 may be constructed as an elongated hole, in order to be able to carry out a compression. So as to lock or secure of the intramedullary nail 1, screws (not shown) may be inserted into the locking holes 9 in the region of the proximal end part 2.

In the region of the distal end part 3, there may be one to four locking holes 10, 12 which extend transversely to the central axis 6. These locking holes 10, 12 may be disposed in different radial directions and enclose different angles with one another. Moreover, the distances between the central locking hole 12 and the other two locking holes 10 may be different. In one embodiment, there may be two locking holes, which extend transversely to the central axis and enclose with one another an angle preferably of about 45° to 90°. In another embodiment, the distal end part 3 may have three locking holes, where the distance between the central locking hole and the other two locking holes is different.

A cannulated, intramedullary nail may be implanted in the method described below. The method includes the steps of first bringing about and maintaining the optimum setting which depends on the type of fracture. Next, opening the medullary canal of the of the bone in which the intramedullary nail is to be inserted with the help of an opening instrument, so that the entry angle and the orientation with respect to the medullary canal are correct. The entry angle and orientation may depend on the surgical technique used. A guide wire is introduced into the distal, future end position of the intramedullary nail. In this step, determination of the length of the intramedullary nail required. The intramedullary nail, pre-mounted on an insertion handle is brought by means of the guide wire through the opening channel into the medullary space. After the axial position of the intramedullary nail is checked and repositioned, the intramedullary nail is locked/secured in place by various locking options, for example screws inserted through the locking holes described above.

It is contemplated that the features of the above embodiments of the intramedullary nail may be combined in a number of combinations to produce derivative embodiments. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An intramedullary nail comprising:
 an elongated body extending along a central longitudinal axis and including:
 a straight proximal end portion;
 a straight distal end portion extending proximally from a distal end of the nail by a predetermined length; and
 a central portion extending proximally from a proximal end of the distal end portion to a distal end of the proximal end portion, wherein the central portion includes a first curved portion having a first length with a first radius of curvature, and a second curved portion having a second length shorter than the first length and a second, non-zero radius of curvature smaller than the first radius of curvature.

2. The intramedullary nail of claim 1, wherein the second curved portion is positioned proximally of the first curved portion.

3. The intramedullary nail of claim 1, wherein the first and second curved portions lie in the anatomical medio-lateral plane in an operative configuration.

4. The intramedullary nail of claim 1, wherein the proximal end portion axially adjoins the second curved portion and is straight.

5. The intramedullary nail of claim 1, wherein the first curved portion has a radius of curvature ranging from about 300 to about 1300 mm.

6. The intramedullary nail of claim 1, wherein the intramedullary nail has a total length ranging from 200 to 500 mm.

7. The intramedullary nail of claim 1, wherein tangents at two end points of the central portion, including the first and second curved portions enclose an angle gamma between about 9° and about 12°.

8. The intramedullary nail of claim 7, wherein tangents at two end points of the first curved portion enclose an angle alpha ranging from about 7° to about 10°.

9. The intramedullary nail of claim 8, wherein the angle alpha ranges from about 8° to about 9°.

10. The intramedullary nail of claim 7, wherein tangents at two end points of the second curved portion enclose an angle beta ranging from about 1° to about 3°.

11. The intramedullary nail of claim 1, wherein a ratio of the total length of the intramedullary nail to the radius of the first curved portion ranges from about 0.2 to about 0.8.

12. The intramedullary nail of claim 1, wherein a length of the proximal end portion ranges from ⅙ to ⅓ of the total length of the intramedullary nail.

13. The intramedullary nail of claim 1, wherein a length of the distal end portion ranges between about 0.20 to about 0.55 of the total length of the intramedullary nail.

14. The intramedullary nail of claim 1, wherein the first curved portion has a length ranging from about 0.2 to about 0.4 of the total length of the intramedullary nail.

15. The intramedullary nail of claim 1, wherein the distal end portion has a length about 0.25 of the total length of the intramedullary nail.

16. The intramedullary nail of claim 1, further comprising a longitudinal borehole extending through the body, a borehole axis of the borehole being coaxial with the central longitudinal axis.

17. The intramedullary nail of claim 1, further comprising:
a first locking hole provided in the proximal end portion, a first locking hole axis of the first locking hole extending transversely to the central longitudinal axis; and
a second locking hole provided in the distal end portion, a second locking hole axis of the second locking hole extending transversely to the central longitudinal axis.

18. The intramedullary nail of claim 17, further comprising a third locking hole provided in the distal end portion, a third locking hole axis of the third locking hole extending transversely to the central longitudinal axis, the second and third locking hole axes enclosing an angle of about 45° to about 90°.

19. The intramedullary nail of claim 18, further comprising a fourth locking hole provided in the distal end portion, a fourth locking hole axis of the fourth locking hole extending transversely to the central longitudinal axis, wherein a distance between adjacent ones of the second, third and fourth locking holes are different from one another.

20. The intramedullary nail of claim 1, wherein the second curved section has a radius ranging from about 10 to about 50 mm.

* * * * *